United States Patent [19]

Palla et al.

[11] Patent Number: 4,661,599

[45] Date of Patent: Apr. 28, 1987

[54] THIAZOLINE COMPOUNDS EXERTING A ANTIDOTAL ACTIVITY FOR THE DEFENSE OF AGRARIAN CULTIVATIONS FROM THE ACTION OF NON-SELECTIVE HERBICIDES

[75] Inventors: Ottorino Palla, Crema; Giovanni Camaggi, Lodi; Franco Gozzo, San Donato Milanese; Augusto Menconi, Crema; Ernesto Signorini, Malnate, all of Italy

[73] Assignee: Montedison S.p.A., Milan, Italy

[21] Appl. No.: 688,902

[22] Filed: Jan. 4, 1985

[30] Foreign Application Priority Data

Jan. 6, 1984 [IT] Italy ................................ 19047 A/84

[51] Int. Cl.[4] .................. C07D 277/10; C07D 263/12; A01N 43/76; A01N 43/78
[52] U.S. Cl. ........................................ 548/146; 71/90; 548/215
[58] Field of Search ................................ 548/146, 215

[56] References Cited

U.S. PATENT DOCUMENTS 4,320,069 3/1982 Statton et al. ................ 260/453 SP

FOREIGN PATENT DOCUMENTS 57-116278 12/1982 Japan .................................. 548/146

OTHER PUBLICATIONS

Litt et al., *Chemical Abstracts*, vol. 65:10689d, 1966.
Scherer et al.; *Chemical Abstracts*, vol. 73:45495p, 1970.

*Primary Examiner*—Robert Gerstl
*Assistant Examiner*—Stephen M. Kapner
*Attorney, Agent, or Firm*—Stevens, Davis, Miller & Mosher

[57] ABSTRACT

There are described compounds exerting an antidotal activity belonging to the classes of the 2-thiazolines-2-substituted and 2-oxazolines-2-substituted, useful in the defense of agrarian cultivations from the toxic action of non-selective herbicides. Utilization and preparation methods thereof are described as well.

5 Claims, No Drawings

THIAZOLINE COMPOUNDS EXERTING A ANTIDOTAL ACTIVITY FOR THE DEFENCE OF AGRARIAN CULTIVATIONS FROM THE ACTION OF NON-SELECTIVE HERBICIDES

This invention relates to a new class of derivatives of 2-thiazoline and of 2-oxazoline endowed with an antidotal action towards non-selective herbicides in important agrarian cultivations. Furthermore, the invention relates to a method of defending agrarian cultivations from the toxic action of non-selective herbicides, consisting in administering the compounds of the invention to the cultivations, and to the compositions of agrarian use containing said compounds.

As is known, the herbicides belonging to the classes of chloroacetanilides, thiolcarbamates, triazines etc. are useful compounds in the fight against the infesting plants of important agrarian cultivations.

However, many of such herbicides exert their toxic action also towards certain useful cultivations, such as, for example, maize and sorghum, and by consequence, since they are non-selective, they cannot be used for the weed killing of such cultivations.

The availability of antidotes, i.e. of compounds which defend the useful cultivations from the action of the herbicides without reducing at the same time the herbicidal activity towards infesting plants, permits to use these herbicides also for protecting those useful cultivations which otherwise would be damaged.

Among the main herbicides which prove phytotoxic for certain useful cultivations there may be cited the ones belonging to the class of the chloroacetanilides, which includes, for example, N-methoxymethyl-2,6-diethyl-chloroacetanilide (common name: Alachlor), N-butoxymethyl-2,6-diethyl-6-allyl-chloroacetanilide (item M8669), and the ones belonging to the class of the thiolcarbamates, which includes for example N,N-diisopropyl-S-(2,3-dichloroallyl)-thiolcarbamate (common name Triallate); N,N-diethyl-S-(4-chlorobenzyl)-thiolcarbamate (common name Benthiocarb); N,N-dipropyl-S-ethyl-thiolcarbamate (common name Eptam).

There are known compounds belonging to various chemical classes, which are capable of protecting useful cultivations from the toxic action of herbicides. For example, dichloroacetamides useful as antidotes have been described in U.S. Pat. No. 4,021,224 (Stauffer) and in U.S. Pat. No. 4,228,101 (Montedison).

We have now found a new class of antidotes— this being the object of the present invention—consisting of the compounds having general formula (I):

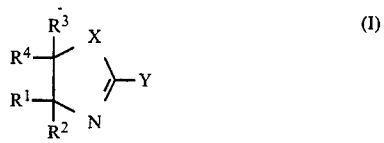

wherein:
$X = S, O$;
$Y$ = alkyl $C_1$–$C_4$ substituted by one or more halogen atoms (Cl, Br, F);
$R^1$, $R^2$, $R^3$ and $R^4$, like or unlike one another, are hydrogen, alkyl $C_1$–$C_4$.

The toxic action of non-selective herbicides, belonging for example to the class of chloroacetanilides and of thiolcarbamates, towards useful cultivations can be highly reduced or eliminated without losing at the same time the herbicidal action towards infesting plants, if the compounds of formula I are utilized as antidotes.

Thus, a further object of the present invention consists in a method of reducing the damages to useful plants caused by non-selective herbicides belonging e.g. to the class of the chloroacetanilides or of the thiolcarbamates, such method consisting in treating the plants or the soil in which they grow with an effective amount of an antidote of formula I, either as such or as a suitable composition.

Another object of this invention is represented by compositions containing a compound of formula I as an active ingredient besides inert carriers and optionally herbicides and other additives, useful for treating the seeds of useful plants, the plants themselves or the ground in which they grow.

A further object of the present invention are the seeds of useful plants when treated with an effective amount of a compound of formula I The compounds of formula I are prepared according to general methods adopted in the synthesis of 2-thiazolines. For example, it is possible to employ the Ritter reaction between a nitrile and a diol or a 2-mercaptoalcohol (Organic Reactions, vol. 17 (1969), 237) according to the following equation:

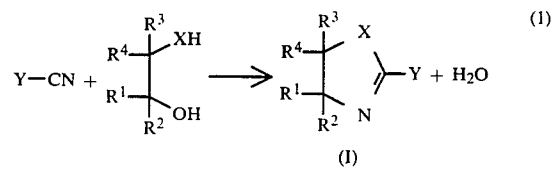

wherein X, Y, $R^1$, $R^2$, $R^3$ and $R^4$ are the same as defined hereinabove.

In particular, when $X = O$, the compounds of formula (I) are also obtainable by reacting a haloid salt with a 2-halo-alkylamine with the proper anhydride (Gabriel, B. 22, 2221) according to the equation:

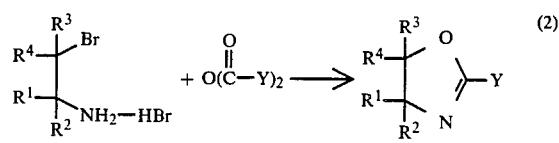

Still in particular, when $X = S$, the compounds of formula (I) are obtainable by reacting a disulphide corresponding to 2-mercaptoalkylamine with the proper anhydride (Gabriel, B. 24, 1117) according to the equation:

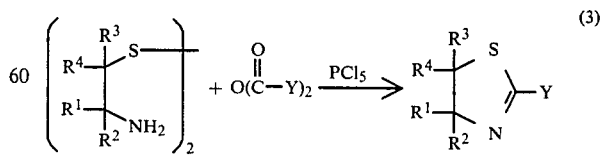

At last, another general method which is very useful for synthetizing the compounds (I) in which $X = S$, consists in treating a nitrile with a 2-mercaptoalkylamine according to the equation:

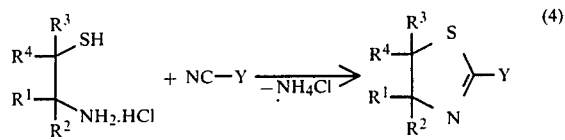

This reaction is suitably conducted in an alcoholic solvent, for example methanol or ethanol, in reflux conditions.

As mentioned hereinbefore, the antidotes of formula (I) exert a remarkable antidotal action which is by far superior to the one of antidotes of the art, for example to the action of antidote N,N-diallyldichloroacetamide (R-25788) described in the above-cited U.S. Pat. No. 4,021,244 (comparative example No. 4).

The antidotes of formula (I) can be applied to the useful cultivations according to different modalities.

For example, they can be utilized for a preventive dressing of the seeds, so that the plant which will develop from said seeds may be protected against the toxic action of non-selective herbicides.

As an alternative, the compounds of formula (I) can be used for treating the plant itself or the soil in which it grows. In this case the antidotes can be distributed either alone or preferably combined with the nonselective herbicide.

The various kinds of application require different conditions which influence the practical aspects of the treatment, such as antidote amount, treatment period and type of composition.

Other factors influencing the practical aspects of the treatment are the type of cultivation to be protected, the non-selective herbicide which is used, climatic and environmental conditions.

When the antidote is utilized in a preventive dressing of the seeds, it can be employed as such or preferably in the form of a suitable composition.

The compositions for the dressing of the seeds may be in the form of powders, wettable powders or emulsifiable concentrates and generally consist of the active compounds in amounts ranging from 0.5 to 95% by weight and of the usual inert carriers which, depending on the type of composition, may be solid, such as talc, silica, diatom earth, bentonite, alkyl-aromatic hydrocarbons, acetone, cyclohexanone and mixtures thereof.

Also proper additives, such as surfactants, wetting agents, dispersants and mixtures thereof can be present in the compositions.

A specific example of a composition in powder for the seed dressing is the following:
  compounds of formula (I): 25-75% by weight
  mixture of a wetting agent, a dispersant and an adhesion promoting agent: 1-5% by weight
  solid inert carrier: 20-74% by weight.

Some examples of useful wetting agents are polyoxyethylated nonyl-phenols, sodiumalkylnaphthalensulphonates, sodium alkylsulphosuccinates; some examples of dispersants are lignosulphonates of sodium, calcium or aluminium, sodium alkylnaphthalensulphonates condensed with formaldehyde, maleic anhydride/diisobutylene copolymers; some examples of adhesion promoting agents are glycols, glycerine, polyglycols, arabic gum, starch, sodium polymethacrylate with different molecular weight.

All these additives are well known in the formulative field and are commercially available also in already prepared mixtures.

The abovesaid compositions are preapred by mixing the ingredients and by homogenizing them by means of grinding until obtaining the desired particle size.

Such compositions may be used as such for the dry seed-dressing, or may be diluted with some water for the wet seed-dressing.

As indicated hereinabove, the antidote amount to be distributed onto the seeds varies as a function of various factors; however, it is generally sufficient to use product amounts ranging from 0.1 to 100 g/kg of seed.

Of course, the treatments carried out directly on the plant or in the medium in which it grows require the use of the antidote in the form of a suitable composition according to the praxis which is usual for this kind of application.

In the applications in which the antidote is distributed onto the vegetation or in the earth along with the non-selective herbicide in the same formulation, the type of formulation and the content vary both in relation to the facts explained hereinbefore and in relation to the type of herbicide employed and to the characteristics thereof.

The antidote amount to be utilized generally ranges from 0.03 to 10 parts by weight for each 100 parts by weight of herbicide.

Besides maize, among the cultivations which can be defended from the toxic action of non-selective herbicides thanks to the use of antidotes of formula (I), there may be cited beet, sorghum and wheat.

In order to better illustrate the present invention, the following examples are given.

EXAMPLE 1

Preparation of 2-trichloromethyl-2-thiazoline [Compound No. 1]

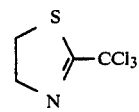

5.65 g (0.05 moles) of 2-mercaptoethylamine hydrochloride and 7.2 g (0.05 moles) of trichloroacetonitrile in 50 ml of methanol were heated at reflux during 3 hours. At the end of this step the solvent was distilled off at reduced pressure and the residual oil was diluted with 100 ml of diethylether.

The ammonium chloride which had formed during the reaction was separated by filtration and the ethereal solution, after washing with water, drying with $Sa_2SO_4$ and evaporation of the solvent, provided 9 g (0.044 moles) of the product to be obtained, in the form of a liquid having a boiling point of 95°–100° C. (20 mm HG), I.R.: $\nu$ (C=N) 1615 cm$^{-1}$.

EXAMPLE 2

Preparation of 2-dichloromethyl-2-thiazoline (M13302) [Compound No. 2]

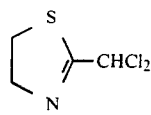

Starting from dichloroacetonitrile and by means of a process analogous with the one described in example 1, the compound indicated in the title and having the following characteristics was prepared:

Physical state: pale-yellow oil.
I.R.: $\nu$ (C=N) 1620 cm$^{-1}$.
1H-NMR (CDCl$_3$).

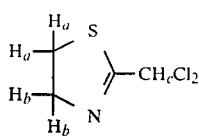

$\delta$ (ppm): H$_a$ 3.48 (2H, triplet, J = 8 Hz)
H$_b$ 4.36 (2H, triplet, J = 8 Hz)
H$_c$ 6.52 (1H, singlet).

EXAMPLE 3

Determination of the antidotal activity for the treatment of the soil.

The test was carried out on maize of variety Decalbe XL 72 A properly sowed into pots containing sandy soil.

The sowed pots were divided into three groups. A group was treated by spraying the soil with a composition containing herbicide Eptam (in a dose corresponding to 8 kg/ha of active substance), to which the compound of formula (I) to be tested at the selected concentration was added; a second group was treated only with the herbicide, while the third group was treated neither with the herbicide nor with the antidote and was used as a check.

The pots were kept in a conditioned room (spring-growth conditions) at 15°-24° C., 70% of relative humidity, 12-hour photoperiod, and were regularly sprinkled to secure a good germination.

10 days after the treatment, the antidotal activity was evaluated by comparing the plant and the vegetative state thereof with the plants treated with the herbicide only and with the ones not treated at all.

The results were expressed on the basis of the plant's vegetative state according to a scale of values from 4 (complete stop of the growth or death of the plant) to 0 (sound plant, growth like that of the check grown in the absence of both herbicide and antidote). By consequence, a numerical evaluation like that of the plants treated with the herbicide only indicates the absence of the antidotal effect, and an evaluation equal to zero indicates a full protection of the plant from the toxic action exerted by the herbicide; the intermediate values indicate a partial antidotal effect, increasing towards the lower values.

Preliminary laboratory tests indicated that the antidotes of formula (I) are not toxic towards maize, and that the herbicidal activity of Eptam towards the common infesting plants of Maize (*Solanum nigrum*, *Amarantus* spp., *Echinochloa* spp., *Digitaria* spp., *Setaria* spp., *Sorghum halepense*, *Panichum dichotomiflorum*, *Cyperus rotundus* and *Cyperus esculentus*) is not affected by the presence of the antidote in this kind of test.

The compounds of examples 1 and 2 (No. 1 and No. 2 respectively) exhibited a full antidotal activity (growth of the plant equal to the one of the check, evaluation=0) at a dose of 400 g/ha (5% by weight in respect of the herbicide), while in the absence of the antidote, herbicide Eptam, at the considered dosage, caused a complete stop in the plants' development (evaluation=4).

EXAMPLE 4

Determination of the antidotal activity of Compound No. 2 at various doses for the treatment of the soil in the defense of maize.

Following the same modalities described in example 3, but using increasing doses of the compounds being tested, the results recorded in the following Table and expressed as % of defense from the phytotoxic action of Eptam were obtained.

TABLE I

| Compound | Doses g/h | % referred to herbicide (Eptam = 8 kg/ha) | Activity defence in % |
|---|---|---|---|
| No. 2 | 24 | 0.3 | 100 |
| (M 13302) | 12 | 0.15 | 100 |
|  | 6 | 0.075 | 100 |
| R-25788 | 24 | 0.3 | 90 |
| (check | 12 | 0.15 | 50 |
| compound) | 6 | 0.075 | 10 |

What is claimed is:

1. A compound of formula:

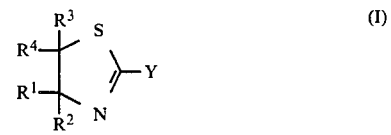

wherein:
Y is an alkyl C$_1$–C$_4$ substituted by at least one halogen atom selected from the group consisting of Cl, Br and F; and
R$^1$, R$^2$, R$^3$ and R$^4$, the same or different, are selected from the group consisting of hydrogen and a C$_1$–C$_4$ alkyl.

2. The compounds according to claim 1, in which Y=CHCl$_2$.

3. The compounds according to claim 2, in which R$^1$, R$^2$, R$^3$ and R$^4$ are H.

4. A compound according to claim 1 and which is 2-dichloromethyl-2-thiazoline.

5. A compound according to claim 1 and which is 2-trichloromethyl-2-thiazoline.

* * * * *